(12) United States Patent
Modai et al.

(10) Patent No.: US 11,259,758 B2
(45) Date of Patent: Mar. 1, 2022

(54) ENHANCED COMMUNICATION WITH AN APPLICATION SERVICE PROVIDER BASED ON MEDICAL TELEMETRY COLLECTED BY A USER DEVICE

(71) Applicant: Avaya Inc., Basking Ridge, NJ (US)

(72) Inventors: Ori Modai, Ramat Hasharon (IL); John Yoakum, Cary, NC (US)

(73) Assignee: Avaya, Inc., Basking Ridge, NJ (US)

( * ) Notice: Subject to any disclaimer, the term of this patent is extended or adjusted under 35 U.S.C. 154(b) by 70 days.

(21) Appl. No.: 14/673,440

(22) Filed: Mar. 30, 2015

(65) Prior Publication Data

US 2016/0287189 A1 Oct. 6, 2016

(51) Int. Cl.
| | |
|---|---|
| *A61B 5/00* | (2006.01) |
| *G16H 50/20* | (2018.01) |
| *G16H 80/00* | (2018.01) |
| *G16H 40/67* | (2018.01) |
| *A61B 5/021* | (2006.01) |
| *A61B 5/11* | (2006.01) |
| *A61B 5/145* | (2006.01) |
| *A61B 5/01* | (2006.01) |

(Continued)

(52) U.S. Cl.
CPC ............ *A61B 5/747* (2013.01); *A61B 5/0022* (2013.01); *A61B 5/6898* (2013.01); *G16H 40/67* (2018.01); *G16H 50/20* (2018.01); *G16H 80/00* (2018.01); *A61B 5/01* (2013.01); *A61B 5/021* (2013.01); *A61B 5/02055* (2013.01); *A61B 5/02438* (2013.01); *A61B 5/1123* (2013.01); *A61B 5/14532* (2013.01)

(58) Field of Classification Search
CPC .. G06F 19/3418; G06F 19/34; G06F 19/3406; G06F 19/321; G06F 19/322; G06F 19/3431; G06F 19/345; G06F 19/3456; G06F 19/3481; G06F 19/19; A61B 5/0022; A61B 5/1442; A61B 5/00; A61B 5/0024; A61B 5/0205; A61B 5/021; A61B 5/681; A61B 2505/03; A61B 5/0006; A61B 5/0008; A61B 5/0215; A61B 5/0404; A61B 5/4806; A61B 5/4833; A61M 2021/0072; A61M 2021/0083; A61M 21/00
See application file for complete search history.

(56) References Cited

U.S. PATENT DOCUMENTS 9,368,014 B1 * 6/2016 Bittman ............. G08B 21/0453
10,431,336 B1 * 10/2019 Murrish ................. G16H 20/10
(Continued)

*Primary Examiner* — Amine Benlagsir

(57) ABSTRACT

Embodiments disclosed herein provide methods, systems, and computer readable storage media for facilitating enhanced communication with an application service provider based on medical telemetry collected by a user device. In a particular embodiment, a method provides collecting medical telemetry of a user of the user communication device and processing the medical telemetry to identify abnormalities therein. Upon identifying at least one abnormality in the medical telemetry, the method provides determining whether the at least one abnormality indicates that the user is experiencing a health issue. After determining that the at least one abnormality indicates that the user is experiencing the health issue, the method provides transferring a health notification indicating the health issue to the application service provider.

20 Claims, 9 Drawing Sheets

(51) Int. Cl.
*A61B 5/0205* (2006.01)
*A61B 5/024* (2006.01)

(56) References Cited

U.S. PATENT DOCUMENTS

| | | | |
|---|---|---|---|
| 2003/0206116 A1* | 11/2003 | Weiner | A61B 5/1113 340/870.28 |
| 2004/0183668 A1* | 9/2004 | Campbell | G08B 13/19663 340/506 |
| 2009/0069642 A1* | 3/2009 | Gao | A61B 5/02055 600/300 |
| 2009/0089097 A1* | 4/2009 | Schoenberg | G06F 19/3431 705/3 |
| 2009/0182575 A1* | 7/2009 | Warner | G06Q 10/06 705/2 |
| 2010/0106222 A1* | 4/2010 | Lychou | A61N 1/37276 607/60 |
| 2012/0203078 A1* | 8/2012 | Sze | G06F 19/3418 600/301 |
| 2014/0055284 A1* | 2/2014 | Tran | A61B 5/031 340/870.07 |
| 2014/0142963 A1* | 5/2014 | Hill | G06F 19/3418 705/2 |
| 2014/0152466 A1* | 6/2014 | Wiesner | G06F 19/3418 340/870.07 |
| 2014/0203950 A1* | 7/2014 | Zdeblick | G06F 19/3418 340/870.07 |
| 2014/0266787 A1* | 9/2014 | Tran | A61B 5/0022 340/870.07 |
| 2014/0320309 A1* | 10/2014 | Zhang | H04Q 9/00 340/870.07 |
| 2015/0015417 A1* | 1/2015 | Libbus | A61B 5/0006 340/870.07 |
| 2015/0150514 A1* | 6/2015 | Batchinsky | A61B 5/7275 600/301 |
| 2015/0189404 A1* | 7/2015 | Pekarske | H04Q 9/00 340/870.07 |
| 2015/0257647 A1* | 9/2015 | Buck | A61B 5/0028 600/388 |

* cited by examiner

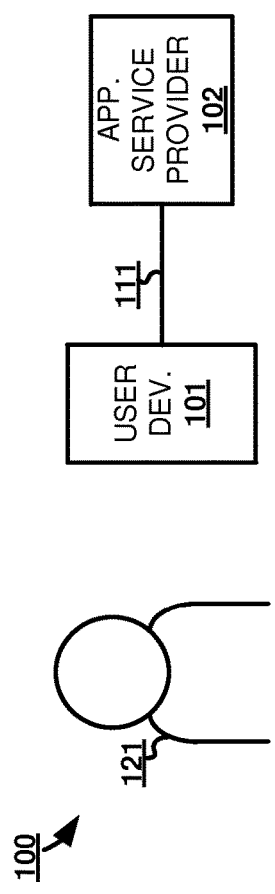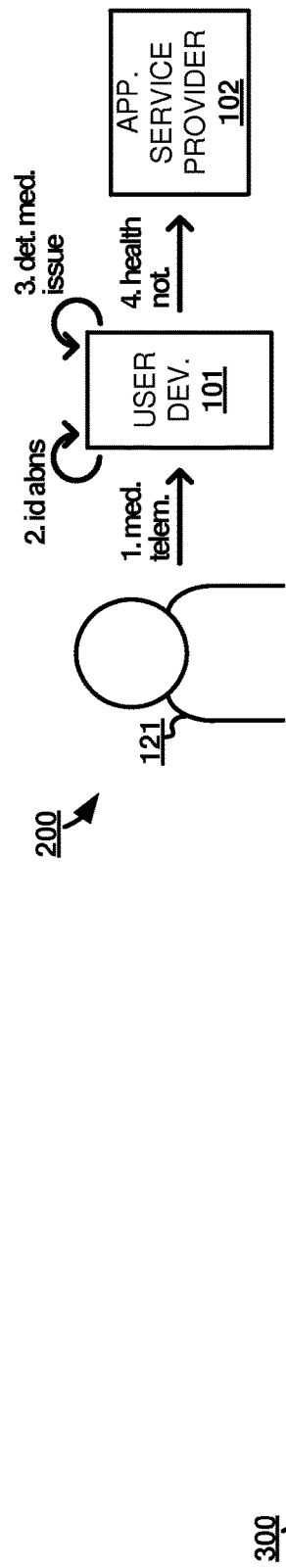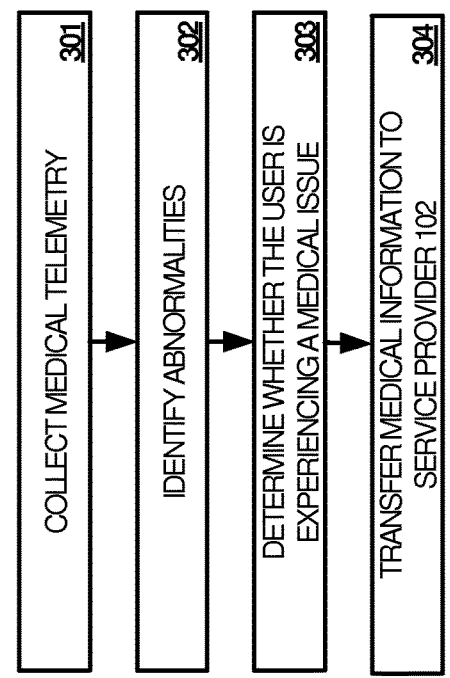

| USER HEALTH PROFILE 900 | |
|---|---|
| BLOOD PRESSURE | 110-135/70-90 |
| HEART RATE | 60-100 BPM |
| BLOOD GLUCOSE | 60-150 mg/dL |
| BODY TEMPERATURE | 96-99° |

Figure 9

ENHANCED COMMUNICATION WITH AN APPLICATION SERVICE PROVIDER BASED ON MEDICAL TELEMETRY COLLECTED BY A USER DEVICE

TECHNICAL BACKGROUND

Telemedicine services have grown substantially in recent years. For example, it is now possible for a doctor to examine a patient over a video communication rather than requiring that patient to visit a medical facility. This and other types of telemedicine have the ability to improve patients, overall quality of life by reducing the time spent in medical facilities, increasing the availability of professional medical caretakers, and increasing the reachability of professional care to rural and developing areas of the world.

While telemedicine services have made great strides to increase health care access to patients, the services still require patient interaction to assess the patient's health. Moreover, depending on the health issue(s) of a particular patient, different health care providers may be better suited to handle the patient's particular issue. Accordingly, a provider best suited to handling the patients issue may not be contacted until after an interaction with the patient makes an initial health issue determination.

With that in mind, many wearable devices now exist that can measure health related telemetry for patients outside of medical facilities, which again allows for added convenience to for a patient. These devices include heart rate monitors, blood pressure monitors, blood sugar monitors, body temperature monitors, and the like. Even though a patient may be provided with telemetry measured by the devices, the telemetry when viewed independently may not mean anything to a patient and, therefore, the patient still requires assessment by a medical professional to determine whether the patent is experiencing a health related issue.

Overview

Embodiments disclosed herein provide methods, systems, and computer readable storage media for facilitating enhanced communication with an application service provider based on medical telemetry collected by a user device. In a particular embodiment, a method provides collecting medical telemetry of a user of the user communication device and processing the medical telemetry to identify abnormalities therein. Upon identifying at least one abnormality in the medical telemetry, the method provides determining whether the at least one abnormality indicates that the user is experiencing a health issue. After determining that the at least one abnormality indicates that the user is experiencing the health issue, the method provides transferring a health notification indicating the health issue to the application service provider.

In some embodiments, after determining that the abnormality indicates that the user is experiencing the health issue, the method provides establishing a user communication with the application service provider.

In some embodiments, the application service provider further uses the medical information to determine at least one of a routing for the user communication and a priority for the user communication.

In some embodiments, compiling medical telemetry of the user comprises receiving medical telemetry captured by a plurality of monitor devices external to the user communication device.

In some embodiments, processing the medical telemetry to identify abnormalities therein comprises comparing the medical telemetry to a profile for the user that indicates normal values for the medical telemetry. An abnormality is identified if a value in the medical telemetry falls outside a corresponding value of the normal values for the medical telemetry.

In some embodiments, processing the medical telemetry to identify abnormalities therein comprises comparing the medical telemetry to medical telemetry patterns that correspond to abnormalities. An abnormality is identified if a pattern in the medical telemetry substantially matches one of the medical telemetry patterns.

In some embodiments, determining whether the at least one abnormality indicates that the user is experiencing the health issue comprises collecting non-medical telemetry of the user and processing the non-medical telemetry and the at least one abnormality to determine whether the abnormality indicates that the user is experiencing the health issue. The abnormality does not indicate that the user is experiencing the health issue if the non-medical telemetry indicates an alternate reason for the at least one abnormality and the abnormality does indicate that the user is experiencing the health issue if the non-medical telemetry does not indicate an alternate reason for the at least one abnormality.

In some embodiments, the method further includes providing the user with an option to override the determination that the at least one abnormality indicates that the user is experiencing the health issue.

In some embodiments, the method further provides receiving information from the application service provider based on the medical information and presenting the information to the user.

In some embodiments, transferring medical information indicating the health issue to the application service provider comprises transferring the health notification in one of a Session Initiation Protocol (SIP) session request or a data channel associated with a WebRTC media connection request.

In another embodiment, a method of operating an application service provider system to handle communications based on medical telemetry is provided. The method includes receiving a health notification about a user from a user communication device. The user communication device transfers the health notification in response to determining that medical telemetry collected by the user communication device includes at least one abnormality that indicates that the user is experiencing a health issue. The method also includes establishing a user communication with the user communication device.

In some embodiments, based on the health notification, the method provides at least one of prioritizing the user communication and routing the user communication.

In some embodiments, the method further includes transferring a request for more detailed medical information to the user communication device and, after the user provides consent, receiving the more detailed medical information from the user communication device.

In some embodiments, the method further includes providing a user profile to the user communication device. The user communication device processes the medical telemetry with the user profile to determine whether the at least one abnormality indicates that the user is experiencing the health issue.

In some embodiments, the method further includes, during the user communication, receiving feedback regarding the health issue, adjusting the user profile based on the feedback, and transferring the adjusted user profile to the user communication device.

In yet another embodiment, an application service provider system for handling communications based on medical telemetry is provided. The application service provider system includes a communication interface and a processing system. The communication interface is configured to receive a health notification about a user from a user communication device and establish a user communication with the user communication device. The user communication device transfers the health notification in response to determining that medical telemetry compiled by the user communication device includes at least one abnormality that indicates that the user is experiencing a health issue. The processing system is configured to determine a routing for the user communication based on the health notification.

In some embodiments, the processing system is configured to prioritize the user communication based on the health notification.

In some embodiments, the communication interface is configured to transfer a request for more detailed medical information to the user communication device and, after the user provides consent, receive the more detailed medical information from the user communication device. The user communication device prompts the user for consent to transfer the more detailed medical information to the application service provider.

In some embodiments, the processing system is configured to generate a user profile. Also, the communication interface is configured to transfer a user profile to the user communication device, wherein the user communication device processes the medical telemetry with the user profile to determine whether the at least one abnormality indicates that the user is experiencing the health issue.

In some embodiments, the application service provider system further includes a user interface configured to receive feedback regarding the health issue during the user communication. The processing system is further configured to adjust the user profile based on the feedback and the communication interface is further configured to transfer the adjusted user profile to the user communication device.

BRIEF DESCRIPTION OF THE DRAWINGS

FIG. 1 illustrates an application service environment for facilitating enhanced communication with an application service provider based on medical telemetry collected by a user device.

FIG. 2 illustrates an operational scenario of the application service environment for facilitating enhanced communication with an application service provider based on medical telemetry collected by a user device.

FIG. 3 illustrates a method of operating the application service environment for facilitating enhanced communication with an application service provider based on medical telemetry collected by a user device.

FIG. 9 illustrates a user health profile for use when facilitating enhanced communication with an application service provider based on medical telemetry collected by a user device.

DETAILED DESCRIPTION

Figure 4:
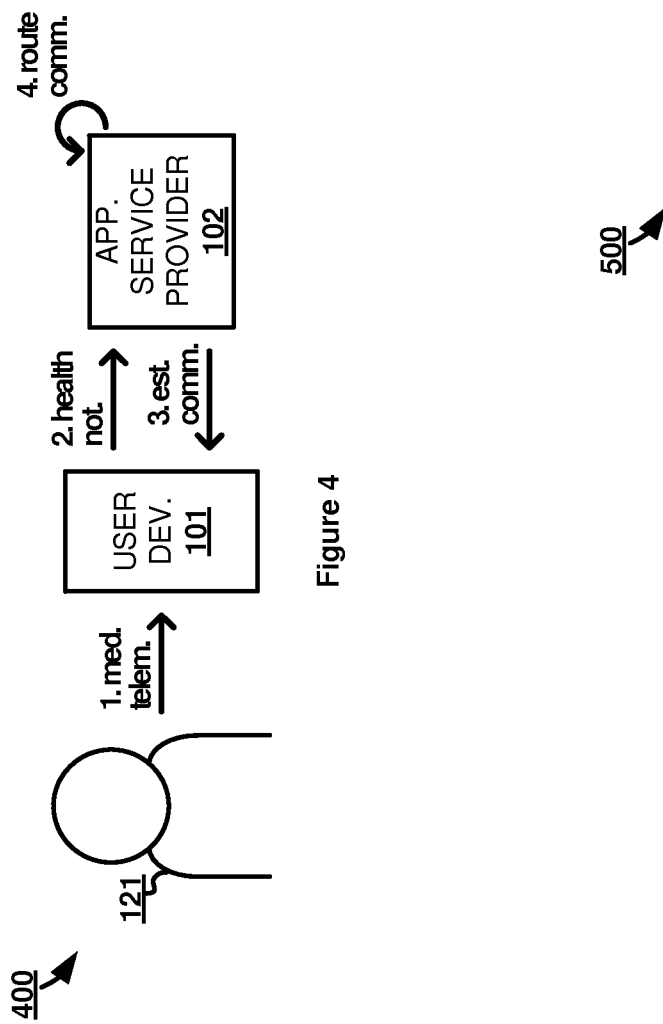
FIG. 4 illustrates an operational scenario of the application service environment for facilitating enhanced communication with an application service provider based on medical telemetry collected by a user device.

The following description and associated figures teach the best mode of the invention. For the purpose of teaching inventive principles, some conventional aspects of the best mode may be simplified or omitted. The following claims specify the scope of the invention. Note that some aspects of the best mode may not fall within the scope of the invention as specified by the claims. Thus, those skilled in the art will appreciate variations from the best mode that fall within the scope of the invention. Those skilled in the art will appreciate that the features described below can be combined in various ways to form multiple variations of the invention. As a result, the invention is not limited to the specific examples described below, but only by the claims and their equivalents.

Wearable devices may now include many different types of health related sensors. Heart rate monitors, blood pressure monitors, temperature monitors, and glucose monitors are just a few of the possible sensors that modern wearable devices are capable of incorporating. These sensors may be part of single purpose wearable devices or may be incorporated into wearable devices having other functions. The wearable devices may take the form of a smartphone, watch/bracelet, chest strap, belt clip, armband, or any other form that allows a person to carry the device on their body.

While the information captured by the health sensors described above may be easily interpreted by a health care professional, a typical user of the wearable devices containing those health care sensors may not have the expertise to interpret the captured information and, even if they did have the expertise, they may not be constantly monitoring the information. Moreover, if the user is in contact with a healthcare professional, the user must describe the captured information to the healthcare professional for analysis. Then, if the analysis identifies a health issue for the user, the user may need to be transferred to someone who is better suited to handle the user's health issue.

In contrast, the embodiments described below leverages the information captured by the health sensors in a user's wearable devices to perform continuous, real-time assessment of a user's condition. This assessment not only may be used to notify the user of their health condition but also may be used to notify an application service provider of the user's condition. Such information may be used by the application service provider to proactively reach out to the user based on a health issue indicated by the notification, to route or prioritize an incoming communication from the user to a best suited destination for the communication, to aid a service professional in providing care to the user by using sensor information when assessing and addressing the user's health situation, or for any other reason that may benefit from a knowledge of current health information for a user.

FIG. 1 illustrates application service environment 100. Application service environment 100 includes user communication device 101, application service provider 102, and user 121. User communication device 101 and application service provider 102 communicate over communication link 111. While shown as a direct link, communication link 111 may span various other networks, systems, and devices.

In operation, user communication device 101 may be a cellphone, laptop, tablet, watch, or some other type of computing device capable of exchanging communications with application service provider 102. User device 101 may include one or more sensors that capture medical telemetry, such as heart rate monitors, blood pressure monitors, blood sugar monitors, body temperature monitors, and the like. The sensors included in user device 101 may depend on whether device 101 is a wearable device. As such, though not shown, one or more of the sensors may be included in separate wearable devices in communication with user device 101 (e.g. over Bluetooth, WiFi, or otherwise), including watch(es), armbands, cellphones, chest bands, headsets, or other types of wearable device forms. Additionally, the sensors may be implanted within user 121. For example, a sensor may be built into an implanted pacemaker to report on whether the pacemaker is functioning correctly.

Additionally, user communication device 101 executes software provided by application service provider 102 to monitor the user of user device 101 for health issues. This software may be built into operating software of device 101 or may be an application installed onto device 101 through an app store or otherwise. Application service provider 102 provides backend support for the software on user device 101. Application service provider 102 may provide any type of health related service from simply keeping records of health information received from user device 101 (e.g. on behalf of a user's doctor) to facilitate a communication with the user of user device 101. Thus, application service provider 102 may include data storage and processing systems, call routing equipment (e.g. circuit switched call routers, IP communication routers, and the like), text or video communication servers, workstations (for use by human agents of the application service provider 102), or any other type of system that may be used to provide application services to user communication device 101. Alternatively, application service provider 102 may act as an intermediate system between device 101 and one or more third party service providers, such as an emergency call center (e.g. public service answering point, PSAP), doctor's office, help line, or other type of health related service provider.

FIG. 2 illustrates operation 200 of application service environment 100 to facilitate enhanced communication with an application service provider based on medical telemetry collected by a user device. At step 1, user device 101 collects medical telemetry of its user 121. Medical telemetry includes information related to the health of user 121 and may be received via sensors included in device 101 or included in other wearable devices that are in communication with device 101. Specific examples of medical telemetry include heart rate, blood pressure level, blood sugar level, body temperature, or any other type of health information that can be measured by sensors in user device 101 or in other devices wearable by user 121.

At step 2, the medical telemetry is processed to identify abnormalities therein. The abnormalities may be identified based on single types of medical telemetry or may also be identified based on combinations of medical telemetry types. For example, a high heart rate may be an abnormality or a high heart rate in combination with a high blood pressure level may be an abnormality. In some cases, the collected medical telemetry may be compared to defined normal ranges for the telemetry stored in device 101. The normal ranges may be tailored specifically to user 121 or may be more universal ranges.

Upon identifying at least one abnormality in the medical telemetry, step 3 determines whether the at least one abnormality indicates that the user is experiencing a health issue. In some examples, the abnormalities may be compared to information indicating which health issues may be associated with the identified abnormalities. Like the abnormalities, these health issues may be tailored specifically to user 121 or may be more universal. That is, particular abnormalities with respect user 121 may indicate one health issue while the same abnormalities for another user, or in general, may typically indicate a different health issue.

In some cases, the normal ranges for the medical telemetry and definitions for determining whether abnormalities constitute a health issue are included in a profile for user 121. The profile may be generated by a medical professional and transferred to user device 101 for use during steps 2 and 3. The profile may then be subsequently updated should values and definitions therein require changes to better identify abnormalities and health issues. For example, feedback from user 121, a health professional, or otherwise after a false positive for a health issue may help to fine tune the profile and lessen the chance of a false positive in the future.

After determining that the at least one abnormality indicates that user 121 is experiencing the health issue, step 4 transfers a health notification from user device 101 to application service provider 102 indicating the health issue to application service provider 102. The health notification may simply indicate that user 121 is experiencing a health issue or may provide additional details about the health issue, including the health issue itself, the abnormalities that indicated the health issue, information about user 121 (e.g. identification, health conditions, etc.), or any other information relevant to the health of user 121. In some cases, user privacy concerns or privacy regulations, governmental or otherwise, may limit the detail of information that can be included in the health notification.

The health notification may be transferred at the request of user 121 or automatically. Furthermore, depending on the functionality of application service provider 102, the health notification may be transferred during a user communication (e.g. voice, video, or text chat) with an agent at application service provider 102 or a third party (e.g. PSAP for 911 emergency calls) to which the user communication is transferred by application service provider 102, may be transferred upon initiating a communication from user device 101 to provider 102, or may be transferred prior to a communication being initiated, as may be the case if the health notification triggers initiation of a communication to user device 101 from provider 102. Alternatively, application service provider 102 may not be configured to communicate with user 121 and, therefore, does not receive the health notification in correlation with a user communication. For example, application service provider 102 may store the health notification for reference at a later time, may notify user 121's health care provider of the health notification, or perform some other function.

As noted above, application service provider 102 may be incorporated into a larger service provider that has systems and, in some cases, people that can assist user 121. However, application service provider 102 may also act as an intermediary between user device 101 and one or more other service providers. Therefore, in cases of multiple service providers, application service provider 102 may be able to select which service provider is best suited to assist user 121 based on the health notification application and supply information related to the health notification to the selected service provider. For example, if the health notification indicates an emergency health situation, then application service provider 102 may set up a user communication between user device 101 and a 911 operator at a PSAP while providing the PSAP with information related to the health notification. Alternatively, if the health notification does not indicate an emergency, then application service provider 102 may route the health notification (or information gleaned from the health notification) to a different service provider, such as a health help line, automated information logging system, and the like.

Advantageously, operation 200 uses previously independently gathered medical related telemetry to monitor user 121 for health issues in real-time. This not only allows user 121 to be alerted to a health issue they may not otherwise be aware of but also allows application service provider 121 to be aware of the issue in order to provide additional services.

FIG. 3 illustrates a method 300 of operating the application service environment for facilitating enhanced communication with an application service provider based on medical telemetry collected by a user device. Method 300 provides collecting medical telemetry of user 121 of the user communication device 101 (step 301). The medical telemetry may be collected from sensors built into user device 101 or included in other wearable devices in communication with user device 101. Method 300 then provides processing the medical telemetry to identify abnormalities therein (Step 302). Upon identifying at least one abnormality in the medical telemetry, method 300 provides determining whether the at least one abnormality indicates that user 121 is experiencing a health issue (step 303).

In some cases, user device 101 performs steps 302 and 303 independently while, in other cases, may use a remote processing system (e.g. cloud based) to perform at least some of the processing necessary to perform steps 302 and 303. The remote processing system may be included in application service provider 102 but may also be elsewhere. After determining that the at least one abnormality indicates that user 121 is experiencing the health issue, method 300 provides transferring a health notification indicating the health issue to application service provider 102 (step 304). The notification may be transferred from user device 101 or may be transferred from the remote processing system in at least some examples where the remote processing system is used.

FIG. 4 illustrates operation 400 of application service environment 100 to facilitate enhanced communication with an application service provider based on medical telemetry collected by a user device. In step 1, medical telemetry is collected for user 121 by device 101 and device 101 determines that the medical telemetry includes at least one abnormality that indicates that the user is experiencing a health issue. At step 2, application service provider 102 receives a health notification indicating that user 121 is experiencing a health issue.

In this example, application service provider 102 comprises a contact center capable of exchanging communications with user 121 via user device 101. Service provider 102 may communicate using voice calls, video calls, chat communications, or some other communication mode, including combinations thereof. Step 3 determines an appropriate routing for such a user communication based on the health notification. For example, application service provider 102 may be staffed by agents that are trained to assist users with health issues they may be experiencing. The agents may have expertise handling different health care issues. Thus, application service provider 102 determines which agent should handle a communication with user 121 based on the health issue indicated by the health notification from user device 101. Step 5 then initiates and establishes a user communication between user device 101 and the determined agent. Step 4 may be omitted in some examples where routing is not dependent upon information contained in the health notification.

The steps of operation 400 are not necessarily performed in the sequence described. For instance, in some examples, user device 101 may initiate a user communication to application service provider 102 based on the determined health issue. The health notification may be transferred at any point before the user communication is established with an agent such that the health information may be used to select an agent for routing. Additionally, in some examples, the health notification may be used to determine a priority for the user communication with user device 101 should application service provider 102, or a particular agent/agent group of provider 102, be handling a larger number of user communications than it can handle at one time. Thus, more time sensitive medical issues, as indicated by the health notification, may be given priority over less sensitive issues.

Figure 5:
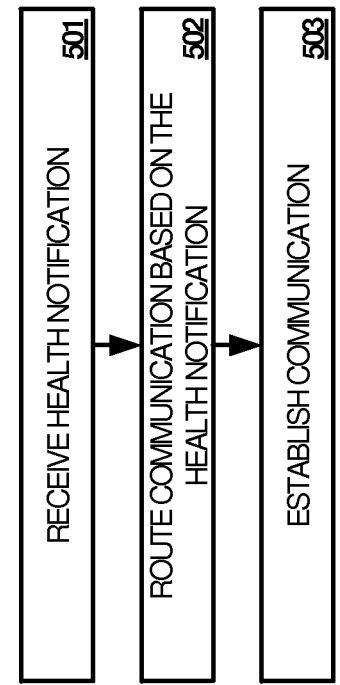
FIG. 5 illustrates a method of operating the application service environment for facilitating enhanced communication with an application service provider based on medical telemetry collected by a user device.

FIG. 5 illustrates a method 500 of operating the application service environment for facilitating enhanced communication with an application service provider based on medical telemetry collected by a user device. Method 500 provides application service provider 102 receiving a health notification about user 121 from user communication device 101 (step 501). User device 101 transfers the health notification in response to determining that medical telemetry collected by user device 101 includes at least one abnormality that indicates that the user is experiencing a health issue. Method 500 then provides routing the user communication based on the health notification (step 502) and establishing the user communication with device 101 based on the routing (step 503). The user communication itself may be initiated by user device 101 or may be initiated by application service provider 102 after application service provider 102 receives the health notification.

Referring back to FIG. 1, user communication device 101 comprises communication circuitry and processing circuitry. The communication circuitry may include wired communication components and/or wireless communication components, such as an amplifier, filter, modulator, and signal processing circuitry. User communication device 101 may also include a user interface, memory device, software, or some other communication components. User communication device 101 may be a telephone, tablet, watch, computer, e-book, mobile Internet appliance, network interface card, media player, game console, or some other communication apparatus, including combinations thereof.

Application service provider 102 comprises a computer system and communication interface. Application service provider 102 may also include other components such as a router, server, data storage system, and power supply. Application service provider 102 may reside in a single device or may be distributed across multiple devices. Specifically, application service provider 102 may include call routing equipment, communication servers, personal computer workstations, network gateway systems, or some other computing system, including combinations thereof.

Communication link 111 uses metal, glass, air, space, or some other material as the transport media. Communication link 111 could use various communication protocols, such as Time Division Multiplex (TDM), Internet Protocol (IP), Ethernet, communication signaling, Code Division Multiple Access (CDMA), Evolution Data Only (EVDO), Worldwide Interoperability for Microwave Access (WIMAX), Global System for Mobile Communication (GSM), Long Term Evolution (LTE), Wireless Fidelity (WIFI), High Speed Packet Access (HSPA), or some other communication format, including combinations thereof. Communication link 111 could be a direct link or may include intermediate networks, systems, or devices.

Figure 6:
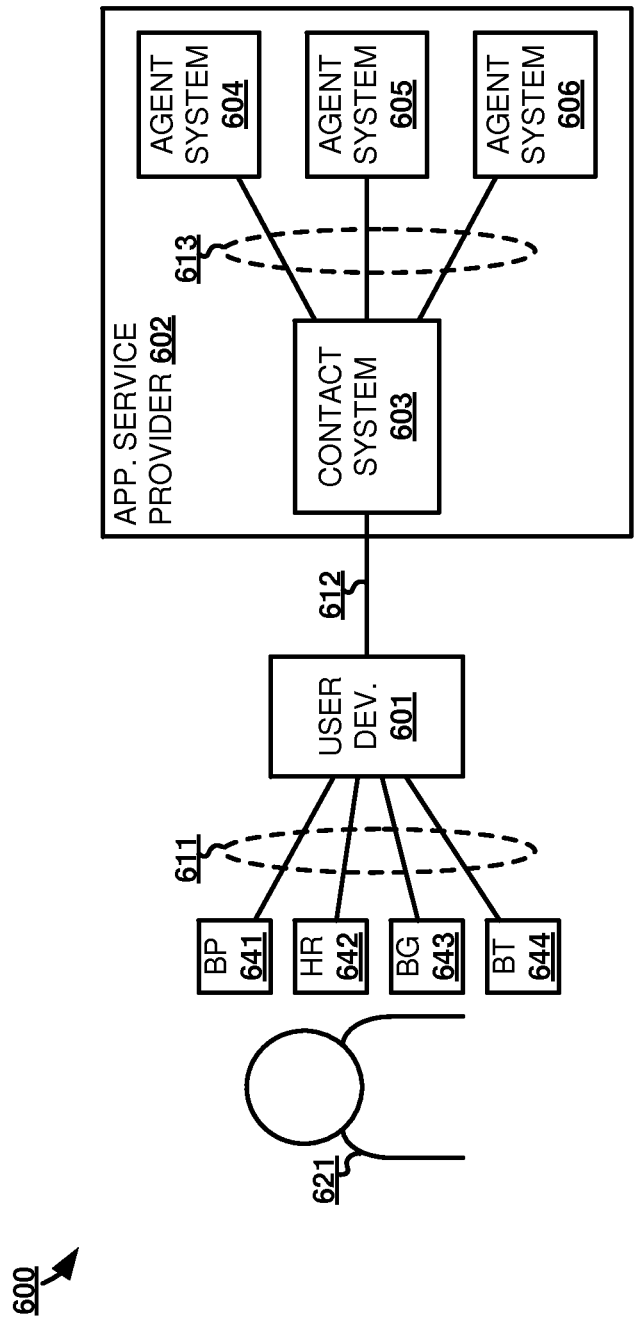
FIG. 6 illustrates another application service environment for facilitating enhanced communication with an application service provider based on medical telemetry collected by a user device.

FIG. 6 illustrates application service environment 600. Application service environment 600 includes user communication device 601, application service provider 602, user 621, blood pressure sensor 641, heart rate sensor 642, blood glucose sensor 643, and body temperature sensor 644. Application service provider 602 includes contact system 603 and agent systems 604-606. Sensor 641-644 and user communication device 601 communicate over one or more communication links 611. User communication device 101 and contact system 603 communicate over communication link 612. Contact system 603 and agent systems 604-606 communicate over communication links 613. While shown as direct links, communication links 111-613 may span various other networks, systems, and devices. Moreover, agent systems 604-606 may not be co-located with each other or with contact system 603. Therefore, agent systems 604-606 may communicate with contact system 603 over one or more communication networks, which may include a communication network, such as the Internet, over which user communication device 601 also communicates with contact system 603.

In this example, application service provider 602 is a contact center for aiding with health care issues. Agents operating agent systems 604-606 may therefore be trained health care professionals that can help users deal with a variety of medical issues and may also be able to send medical services to a user's location should the situation warrant such action. The help is provided over user communications, whether voice, video, text, or other communication mode, between one or more of agent systems 604-606 and user device 601.

To access the services provided by application service provider 602, user 621 executes an application on device 601 that continuously tracks user 621's medical telemetry to determine whether user 621 is experiencing a health issue. Based on the applications directions, user device 601 communicates with sensors 641-644 to collect medical telemetry therefrom. While shown as distinct elements, one or more of sensors 641-644 may be included in the same wearable device. For example, all four sensors may be included in a watch type form factor. Additionally, one or more of the sensors may be incorporated into user device 601. It is entirely possible that, for example, a single watch form factor could include all of sensors 641-644 and perform the functionality of user device 601, as described herein. Another likely form factor example relies on a smartphone type device to act as user device 101, which is in wireless communication (e.g. Bluetooth, Wifi, or otherwise) with sensors 641-644 included in one or more other devices (e.g. the watch described above).

Regardless of the form factor, user device 601 collects the medical telemetry from sensors 641-646 and, should a health issue be identified based on the telemetry, a health notification can be sent to application service provider 602. The health notification may be used to route a communication to or from device 101 or may be presented to and used by an agent at one of agent systems 604-606 to assist in helping user 621 with user 621's health issue. Moreover, the automatic and continuous monitoring of user 621's medical telemetry allows for health issues to be addressed in a timelier manner. This is especially the case if user 621 would not otherwise realize that they are experiencing a health issue.

Figure 7:
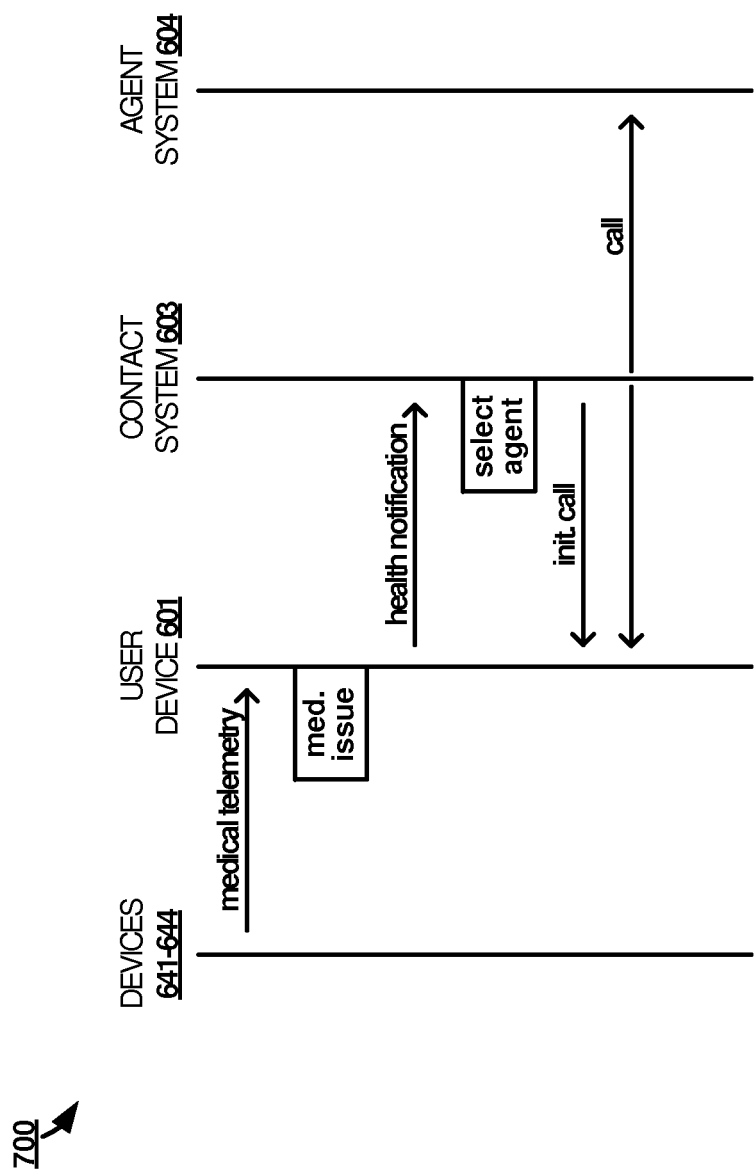
FIG. 7 illustrates an operational scenario of the application service environment for facilitating enhanced communication with an application service provider based on medical telemetry collected by a user device.

FIG. 7 illustrates operation 700 of application service environment 600 to facilitate enhanced communication with an application service provider based on medical telemetry collected by a user device. Specifically, operation 700 describes an example wherein application service provider 602 is configured to reach out to user 621 should user device 601 determine that user 621 is experiencing a health issue. During operation 700, user device 601 continually receives medical telemetry from sensors 641-644. In real-time, the medical telemetry is processed to identify abnormalities in the medical telemetry that indicate user 621 is experiencing a health issue. Different abnormalities may indicate different health issues and more than one health issue may be identified at any time.

Once at least one health issue has been identified, a notification of the health issue is transferred to contact system 603. Upon receiving the health issue notification, contact system 603 determines with which agent system of agent systems 604-606 a voice call should be established. It should be understood that, while this example describes a voice call, contact system 603 may use other communication modes as well or instead. An agent system may be selected based on the skill set of agents operation each respective agent system 604-606. For example, if the health notification indicates an issue involving user 621's heart, then an agent having expertise with heart related matters might be selected.

In this example, contact system 603 selects the agent operating agent system 604 to handle a call with user 621. Thus, contact system 603 initiates a call to user device 601 and, upon user 621 accepting the call, establishes the call between user device 601 and agent system 604. The agent can then communicate with user 621 to assist user 621 with the health issue. In some cases, the agent may use agent system 604 to direct emergency services personnel to user 621's location should such action be deemed necessary.

Figure 8:
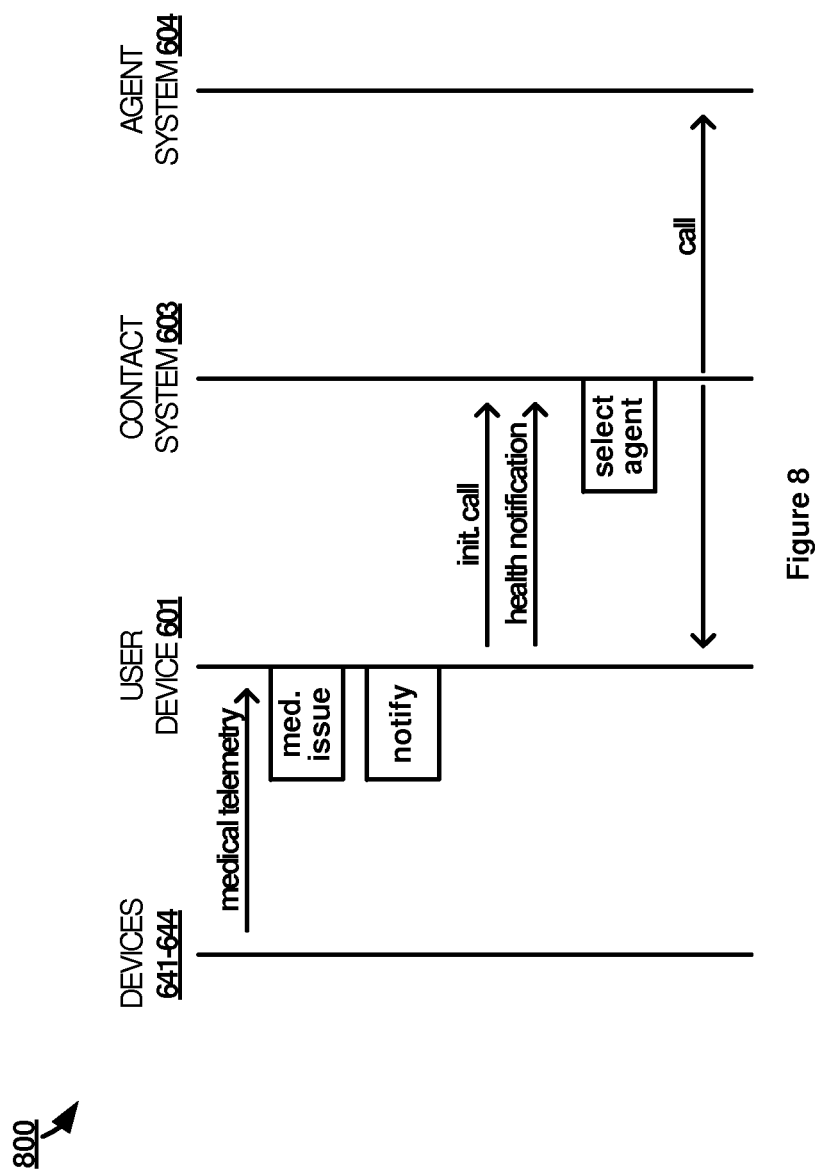
FIG. 8 illustrates another operational scenario of the application service environment for facilitating enhanced communication with an application service provider based on medical telemetry collected by a user device.

FIG. 8 illustrates operation 800 of application service environment 600 to facilitate enhanced communication with an application service provider based on medical telemetry collected by a user device. Specifically, operation 800 describes an example wherein user device 601 is configured to reach out to application service provider 602 should user device 601 determine that user 621 is experiencing a health issue. During operation 800, user device 601 continually receives medical telemetry from sensors 641-644. In real-time, the medical telemetry is processed to identify abnormalities in the medical telemetry that indicate user 621 is experiencing a health issue. Different abnormalities may indicate different health issues and more than one health issue may be identified at any time.

Once at least one health issue has been identified, user device 601 notifies user 621 of the health issue. After notifying the user of the health issue, user device 601 initiates a call to contact system 603 and also transfers a health notification to contact system 603. It should be understood that, while this example describes a voice call, contact system 603 may use other communication modes as well or instead. The call may be initiated in response to an instruction from user 621 to user device 601 after user 621 is notified of the health issue. Thus, user 621 may choose not to place a call for assistance. Alternatively, the call may be initiated automatically upon identifying the health issue. The health notification may be transferred to contact system 603 within a request used to initiate the call. For example, if environment 600 is configured for Session Initiation Protocol (SIP) communications, then the health notification may be included in a SIP session request used to initiate the call. Similarly, if environment 600 is configured for Web Real-Time Communication (WebRTC), then the health notification may be transferred in a data channel associated with a WebRTC media connection request. In some cases, contact system 603 may request the health notification upon receiving a request initiated with the call. Also, in further examples, information (e.g. the health notification or other information) may be requested and exchanged between contact system 603 and user device 601 using Application Programming Interfaces (APIs) for the application running on device 601 that controls the performance of operation 800 and/or APIs for contact system 603.

Upon receiving the health issue notification, contact system 603 determines with which agent system of agent systems 604-606 a voice call should be established. An agent system may be selected based on the skill set of agents operation each respective agent system 604-606. In this example, contact system 603 selects the agent operating agent system 604 to handle a call with user 621. Thus, contact system 603 establishes the call between user device 601 and agent system 604. The agent can then communicate with user 621 to assist user 621 with the health issue. In some cases, the agent may use agent system 604 to direct emergency services personnel to user 621's location should such action be deemed necessary.

During the calls between user device 601 and agent system 604 of operations 700 and 800, the agent may request more detailed information about the user from user device 601. This additional information may be information not included in the health notification due to size constraints on the notification, due to regulatory limits on the type of information that can be provided in a notification of that type, or for some other reason.

In a particular example, a government regulation may indicate that a user must give explicit consent before a health care provider can access personal medical information for the user. Accordingly, agent system 604 (or contact system 603) may automatically, or upon receiving an instruction from the operating agent, transfer a request for more detailed medical information to user device 601. User 621 may then be notified of the request for more detailed information and provided consent by through the user interface of user device 601. Upon receiving consent from user 621, the more detailed information in provided to agent system 604 to further assist user 621 with their health issue. In some cases, user 621 may provide consent prior to receiving any request for more detailed information. As such, the more detailed information can be provided by user device 601 automatically without needing to be requested or immediately upon receiving a request without having to wait for user 621 to consent.

In some embodiments, user device 601 includes or has access to (e.g. located in other devices, wearable or otherwise) other sensors providing telemetry that is not necessarily medical or health related, such as Global Positioning System (GPS) location information, accelerometers, barometers, outside temp, and the like. This other, "non-medical" telemetry may be used to determine whether there is an alternative explanation for identified abnormalities in the medical telemetry. For example, GPS data indicating that user 621 is moving at 6 miles per hour along a path may indicate that the user is running. Thus, if an elevated heart rate is identified as an abnormality, which would normally trigger a heart related health issue, user device 621 may instead determine that user 621 is running based on the GPS data and is not actually experiencing a heart issue. Similarly, while not necessarily sensor data, application data, such as calendar entries, may also be used. That is, the calendar entry may indicate an event going on at the time the abnormality is detected (e.g. spin class) that may explain the abnormality without triggering a health issue notification.

FIG. 9 illustrates a user health profile 900 for use when facilitating enhanced communication with an application service provider based on medical telemetry collected by a user device. User device 601 may use health profile 900 to determine whether abnormalities and health issues exist for user 621. In particular, health profile 900 may take the form of a data structure stored in memory of user device 601. Health profile 900 is a basic profile that includes safe ranges for blood pressure, heart rate, blood glucose, and body temperature. If medical telemetry collected by user device 601 indicates that any of user 621's current medical telemetry values are outside these defined ranges (above or below), then user device 601 will determine an abnormality exists. For example, blood pressure telemetry indicating that user 621's blood pressure is 143/96 falls outside the blood pressure range indicated by health profile 900 and, therefore, constitutes an abnormality.

In the case of profile 900, an abnormality in the medical telemetry would also constitute a health issue (e.g. high blood pressure). However, more detailed profiles may also be used that include definitions for which abnormalities constitute a health issue. These definitions may indicate that abnormalities in multiple types of medical telemetry must exist for a particular health issue (e.g. high blood pressure and high heart rate), may require a pattern to exist either in a single type of medical telemetry or across multiple types (e.g. heart rate stays elevated for a period of time and blood pressure is also up during the same period), or by some other definition.

Figure 10:
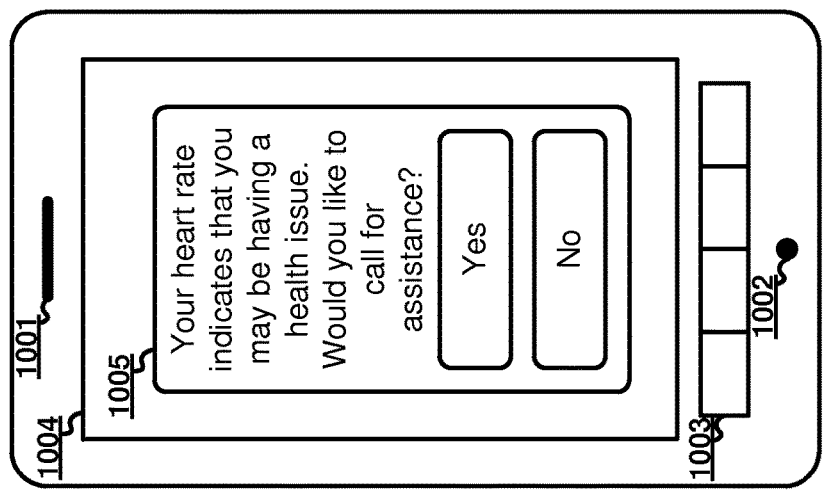
FIG. 10 illustrates a user communication device for facilitating enhanced communication with an application service provider based on medical telemetry collected by a user device.

FIG. 10 illustrates user communication device 1000 for facilitating enhanced communication with an application service provider based on medical telemetry collected by a user device. User communication device 1000 includes speaker 1001, microphone 1002, buttons 1003, and display 1004. User communication device 1000 is a touchscreen device but may be alternatively configured and have more or fewer elements than those depicted.

In this example, display 1004 is presenting notification window 1005 to a user. Notification window 1005 may be presented to the user in operation 800 after a health issue has been determined but before a call is initiated to contact system 603. The user is given the opportunity to select "yes" to call for assistance or "no" to not call for assistance. In some examples, device 1000 may initiate a call after a period of time elapses and no response is received from the user. Thus, if the user is incapacitated device 1000 will automatically call for help. However, by pressing "no", the user can override this automatic call. In other examples, notification window 1105 may not provide the user with an option to override a call but, instead, merely notifies the user that the call (or other type of communication if so configured) is being placed. Other means of overriding the determination that a health notification should be transmitted may also be used. User override functionality allows the user to prevent notifications of false positives from leaving the device. False positives may be caused by bad sensor data, disconnected sensors, improperly processed sensor data, a lack of non-medical telemetry indicating that there is not a health issue, etc.

Figure 11:
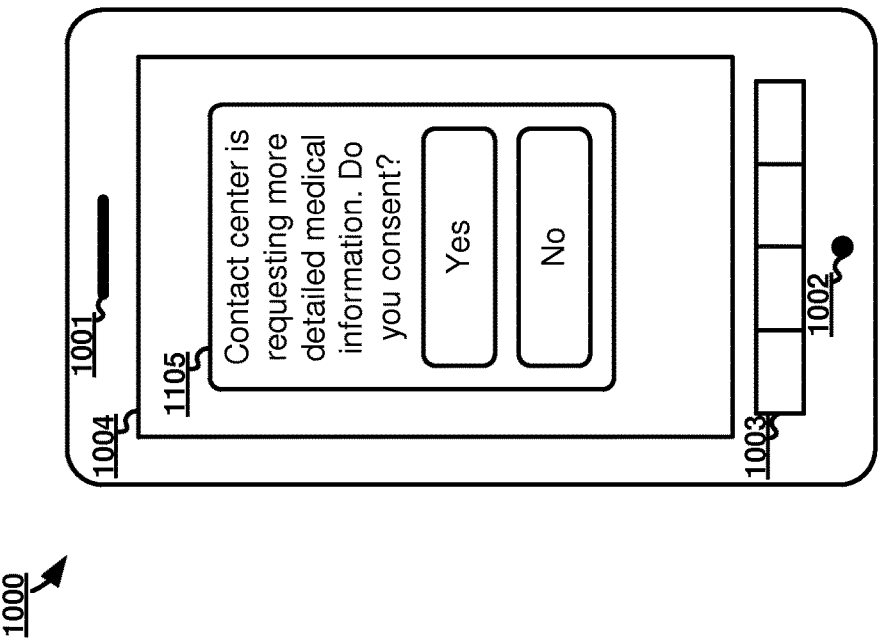
FIG. 11 also illustrates the user communication device for facilitating enhanced communication with an application service provider based on medical telemetry collected by a user device.

FIG. 11 also illustrates user communication device 1000 for facilitating enhanced communication with an application service provider based on medical telemetry collected by a user device. In this example, display 1004 is presenting notification window 1105, which requests consent to transfer more detailed medical information to the contact center. In the context of operations 700 and 800 described above, this notification request may be transferred after a call is established at the request of a contact center agent or automatically by contact system 603. Upon the user selecting "yes", the more detailed medical information is transferred to contact system 603. The user selecting "no", prevents the more detailed medical information from being transferred. As noted above, in some examples, the user may also provide consent for transferring more detailed medical information before any communication is established, which essentially pre-consents to any future request for more detailed information.

By providing user consent, the more detailed information can be presented to and considered by the application service provider assisting with the user's health issue. This more detailed information may include personal information as well as more explicit health information that otherwise may not be able to be included in the initial health notification due to privacy concerns or explicit regulatory requirements. Furthermore, in WebRTC communications or other communication modes that support video, the more detailed information may include video captured of the area surrounding device 1000 by a camera in device 1000. For example, a WebRTC media flow may be invoked to transfer video to an application service provider, which can then use the video information, with or without being viewed by a human agent, to further assess the user's situation.

In further examples, information received from an application service provider may be presented to a user by display 1004. This information may include offers for products or services that may benefit the user, instructions for dealing with the health issue experienced by the user, or any other type of information that may be useful to the user while experiencing a health issue. For example, if an agent at the application service provider determines that a certain over the counter medication would benefit the user, then the agent may direct their system to transfer a message indicating the medication to device 1000. Upon receiving the message, device 1000 displays the message content to the user.

Figure 12:
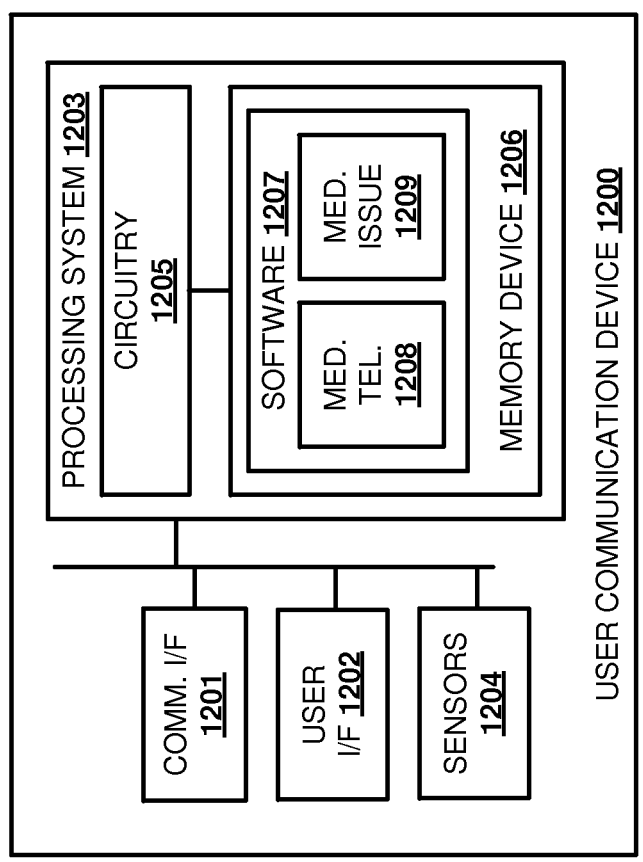
FIG. 12 illustrates another user communication device for facilitating enhanced communication with an application service provider based on medical telemetry collected by a user device.

FIG. 12 illustrates user communication device 1200. User communication device 1200 is an example of user communication devices 101 and 601, although devices 101 and 601 could use alternative configurations. User communication device 1200 comprises wireless communication interface 1201, user interface 1202, and processing system 1203. Processing system 1203 is linked to wireless communication interface 1201 and user interface 1202. Processing system 1203 includes processing circuitry 1205 and memory device 1206 that stores operating software 1207. User communication device 1200 may include other well-known components such as a battery and enclosure that are not shown for clarity. User communication device 1200 may be a telephone, tablet, computer, e-book, mobile Internet appliance, media player, game console, or some other communication apparatus, including combinations thereof.

Communication interface 1201 comprises components that communicate over communication links, such as network cards, ports, RF transceivers, processing circuitry and software, or some other communication devices. Communication interface 1201 may be configured to communicate over metallic, wireless, or optical links. Communication interface 1201 may be configured to use TDM, IP, Ethernet, optical networking, wireless protocols, communication signaling, or some other communication format, including combinations thereof.

User interface 1202 comprises components that interact with a user to receive user inputs and to present media and/or information. User interface 1202 may include a speaker, microphone, buttons, lights, display screen, touch screen, touch pad, scroll wheel, communication port, or some other user input/output apparatus, including combinations thereof. User interface 1202 may be omitted in some examples.

Sensors 1204 comprise heart rate monitors, blood pressure monitors, pedometers, blood glucose monitors, temperature monitors, or any other type sensor for measuring health related information, including combinations thereof. In some embodiments, one or more of the sensors may be located external to user communication device 1200. These external sensors communicate with user communication device 1200 over communication interface 1201. Therefore, sensors 1204 may be omitted in some examples.

Processing circuitry 1205 comprises microprocessor and other circuitry that retrieves and executes operating software 1207 from memory device 1206. Memory device 1206 comprises a non-transitory storage medium, such as a disk drive, flash drive, data storage circuitry, or some other memory apparatus. Processing circuitry 1205 is typically mounted on a circuit board that may also hold memory device 1206 and portions of communication interface 1201 and user interface 1202. Operating software 1207 comprises computer programs, firmware, or some other form of machine-readable processing instructions. Operating software 1207 includes medical telemetry module 1208 and health issue module 1209. Operating software 1207 may further include an operating system, utilities, drivers, network interfaces, applications, or some other type of software. When executed by processing circuitry 1205, operating software 1207 directs processing system 1203 to operate user communication device 1200 as described herein.

In particular, medical telemetry module 1208 directs processing system 1203 to collect medical telemetry of a user of the user communication device and process the medical telemetry to identify abnormalities therein. Upon identifying at least one abnormality in the medical telemetry, health issue module 1209 directs processing system 1203 to determine whether the at least one abnormality indicates that the user is experiencing a health issue. After determining that the at least one abnormality indicates that the user is experiencing the health issue, health issue module 1209 further directs processing system 1203 to transfer a health notification indicating the health issue to the application service provider.

Figure 13:
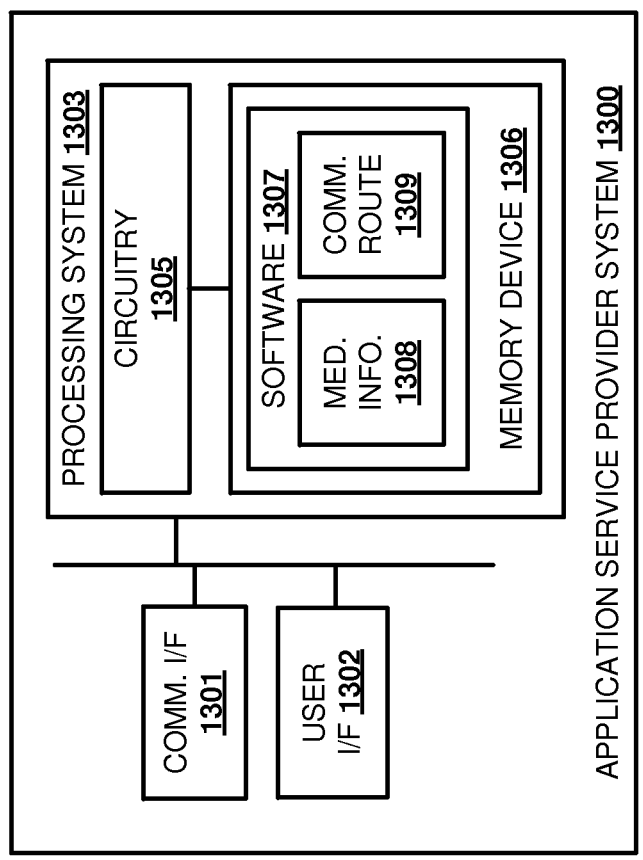
FIG. 13 illustrates an application service provider system for facilitating enhanced communication with an application service provider based on medical telemetry collected by a user device.

FIG. 13 illustrates application service provider system 1300. Application service provider system 1300 is an example of application service provider 103 and contact system 603, although provider 103 and system 603 may use alternative configurations. Application service provider system 1300 comprises communication interface 1301, user interface 1302, and processing system 1303. Processing system 1303 is linked to communication interface 1301 and user interface 1302. Processing system 1303 includes processing circuitry 1305 and memory device 1306 that stores operating software 1307.

Communication interface 1301 comprises components that communicate over communication links, such as network cards, ports, RF transceivers, processing circuitry and software, or some other communication devices. Communication interface 1301 may be configured to communicate over metallic, wireless, or optical links. Communication interface 1301 may be configured to use TDM, IP, Ethernet, optical networking, wireless protocols, communication signaling, or some other communication format, including combinations thereof.

User interface 1302 comprises components that interact with a user. User interface 1302 may include a keyboard, display screen, mouse, touch pad, or some other user input/output apparatus. User interface 1302 may be omitted in some examples.

Processing circuitry 1305 comprises microprocessor and other circuitry that retrieves and executes operating software 1307 from memory device 1306. Memory device 1306 comprises a non-transitory storage medium, such as a disk drive, flash drive, data storage circuitry, or some other memory apparatus. Operating software 1307 comprises computer programs, firmware, or some other form of machine-readable processing instructions. Operating software 1307 includes health notification module 1308 and communication establishment module 1309. Operating software 1307 may further include an operating system, utilities, drivers, network interfaces, applications, or some other type of software. When executed by circuitry 1305, operating software 1307 directs processing system 1303 to operate application service provider system 1300 as described herein.

In particular, health notification module 1308 directs processing system 1303 to receiving a health notification about a user from a user communication device. The user communication device transfers the health notification in response to determining that medical telemetry collected by the user communication device includes at least one abnormality that indicates that the user is experiencing a health issue. Communication establishment module 1309 directs processing system 1303 to establish a user communication with the user communication device.

The above description and associated figures teach the best mode of the invention. The following claims specify the scope of the invention. Note that some aspects of the best mode may not fall within the scope of the invention as specified by the claims. Those skilled in the art will appreciate that the features described above can be combined in various ways to form multiple variations of the invention. As a result, the invention is not limited to the specific embodiments described above, but only by the following claims and their equivalents.

What is claimed is:

1. A non-transitory computer readable storage medium having instructions stored thereon that, when executed by a user communication device, direct the user communication device to perform a method of communicating with a contact center staffed by a plurality of agents, the method comprising:
   collecting medical telemetry of a user of the user communication device;
   processing the medical telemetry to identify abnormalities therein;
   upon identifying at least one abnormality of the abnormalities in the medical telemetry, determining that the at least one abnormality indicates that the user is experiencing a health issue based on identifying a lack of non-medical telemetry indicating a reason, other than the health issue, for the at least one abnormality, wherein the health issue is one of a plurality of health issues that could be indicated by the abnormalities in the medical telemetry;
   in response to determining that the at least one abnormality indicates that the user is experiencing the health issue:
      transferring a health notification indicating the health issue to the contact center, and
      initiating a real-time user communication to the contact center, wherein the contact center uses the health issue indicated by the health notification to identify an agent of the plurality of agents to which the real-time user communication should be directed based on expertise of the agent for handling the health issue and a priority for the real-time user communication relative to other user communications being handled by the contact center, and wherein the real-time user communication comprises a voice call, a video call, or a text chat over which the user and the agent can communicate in real time; and
      establishing the real-time user communication with an agent system operated by the agent.

2. The non-transitory computer readable storage medium of claim 1, wherein the method further comprises exchanging captured communications from the user and the agent over the real-time user communication.

3. The non-transitory computer readable storage medium of claim 1, wherein the priority corresponds to how time sensitive the health issue is relative to other health issues of the other user communications.

4. The non-transitory computer readable storage medium of claim 1, wherein said collecting the medical telemetry of the user comprises:
   receiving the medical telemetry captured by a plurality of monitor devices external to the user communication device.

5. The non-transitory computer readable storage medium of claim 1, wherein said processing the medical telemetry to identify the abnormalities therein comprises:
   comparing the medical telemetry to a profile for the user that indicates normal values for the medical telemetry; and
   wherein the at least one abnormality is identified if a value in the medical telemetry falls outside a corresponding value of the normal values for the medical telemetry.

6. The non-transitory computer readable storage medium of claim 1, wherein said processing the medical telemetry to identify the abnormalities therein comprises:
   comparing the medical telemetry to medical telemetry patterns that correspond to the abnormalities; and wherein the at least one abnormality is identified if a pattern in the medical telemetry substantially matches one of the medical telemetry patterns.

7. The non-transitory computer readable storage medium of claim 1, wherein the method further includes:
collecting the non-medical telemetry.

8. The non-transitory computer readable storage medium of claim 1, wherein the method further comprises:
before initiating the real-time user communication, providing the user with an option to override the determination that the at least one abnormality indicates that the user is experiencing the health issue.

9. The non-transitory computer readable storage medium of claim 1, wherein the method further comprises:
receiving information from the contact center based on the health notification; and
presenting the information to the user.

10. The non-transitory computer readable storage medium of claim 1, wherein said transferring the health notification comprises:
transferring the health notification in one of a Session Initiation Protocol (SIP) session request or a data channel associated with a Web Real-Time Communication (WebRTC) media connection request.

11. A method of operating a contact center system of a contact center staffed by a plurality of agents, to handle communications, the method comprising:
receiving, from a user communication device, a health notification about a user of the user communication device, wherein the user communication device transfers the health notification and initiates a real-time user communication to the contact center in response to determining that medical telemetry collected by the user communication device includes at least one abnormality and determining that the at least one abnormality indicates that the user is experiencing a health issue based on identifying a lack of non-medical telemetry indicating a reason, other than the health issue, for the at least one abnormality, wherein the health issue is one of a plurality of health issues that could be indicated by abnormalities in the medical telemetry, wherein the real-time user communication comprises a voice call, a video call, or a text chat over which the user and an agent of the plurality of agents can communicate in real time, and wherein the health notification indicates the health issue;
using the health issue indicated by the health notification to identify the agent of the plurality of agents to which the real-time user communication should be directed based on expertise of the agent for handling the health issue and a priority for the real-time user communication relative to other user communications being handled by the contact center; and
establishing the real-time user communication between the user communication device and an agent system operated by the agent.

12. The method of claim 11, wherein the priority corresponds to how time sensitive the health issue is relative to other health issues of the other user communications.

13. The method of claim 11, further comprising:
transferring a request for more detailed medical information to the user communication device; and
after the user provides consent, receiving the more detailed medical information from the user communication device.

14. The method of claim 11, further comprising:
providing a user profile to the user communication device, wherein the user communication device processes the medical telemetry with the user profile to determine whether the at least one abnormality indicates that the user is experiencing the health issue.

15. The method of claim 14, further comprising:
during the real-time user communication, receiving feedback regarding the health issue;
adjusting the user profile based on the feedback; and
transferring the adjusted user profile to the user communication device.

16. A contact center system of a contact center staffed by a plurality of agents, for handling communications, the contact center system comprising:
a communication interface configured to receive, from a user communication device, a health notification about a user of the user communication device, wherein the user communication device transfers the health notification and initiates a real-time user communication to the contact center in response to determining that medical telemetry compiled by the user communication device includes at least one abnormality and determining that the at least one abnormality indicates that the user is experiencing a health issue based on identifying a lack of non-medical telemetry indicating a reason, other than the health issue, for the at least one abnormality, wherein the health issue is one of a plurality of health issues that could be indicated by abnormalities in the medical telemetry and wherein the health notification indicates the health issue, and establish the real-time user communication between the user communication device and an agent system operated by an agent of the plurality of agents, and wherein the real-time user communication comprises a voice call, a video call, or a text chat over which the user and the agent can communicate in real time; and
a processing system configured to use the health issue to identify the agent to which the real-time user communication should be directed based on expertise of the agent for handling the health issue and a priority for the real-time user communication relative to other user communications being handled by the contact center.

17. The contact center system of claim 16, wherein the priority corresponds to how time sensitive the health issue is relative to other health issues of the other user communications.

18. The contact center system of claim 16, wherein the communication interface is further configured to:
transfer a request for more detailed medical information to the user communication device, wherein the user communication device prompts the user for consent to transfer the more detailed medical information to the contact center; and
after the user provides consent, receive the more detailed medical information from the user communication device.

19. The contact center system of claim 16, wherein:
the processing system is further configured to generate a user profile; and
the communication interface is further configured to transfer the user profile to the user communication device, wherein the user communication device processes the medical telemetry with the user profile to determine whether the at least one abnormality indicates that the user is experiencing the health issue.

20. The contact center system of claim 19, further comprising:
- a user interface configured to receive feedback regarding the health issue during the real-time user communication;
- wherein the processing system is further configured to adjust the user profile based on the feedback; and
- the communication interface is further configured to transfer the adjusted user profile to the user communication device.

* * * * *